US006824508B2

United States Patent
Kim et al.

(12) United States Patent
(10) Patent No.: US 6,824,508 B2
(45) Date of Patent: Nov. 30, 2004

(54) MICRO ROBOT

(75) Inventors: Byungkyu Kim, Seoul (KR); Jisang Park, Seoul (KR); Kyoung-Dae Kim, Seoul (KR); Yeh-Sun Hong, Seoul (KR); Soo Hyun Kim, Daejeon (KR); Jong-Oh Park, Seoul (KR)

(73) Assignee: Korea Institute of Science and Technology (KR)

( * ) Notice: Subject to any disclaimer, the term of this patent is extended or adjusted under 35 U.S.C. 154(b) by 234 days.

(21) Appl. No.: 10/140,026

(22) Filed: May 6, 2002

(65) Prior Publication Data
US 2002/0171385 A1 Nov. 21, 2002

(30) Foreign Application Priority Data
May 19, 2001 (KR) .......................................... 2001/27494

(51) Int. Cl.$^7$ ................. A61B 1/00; B25J 5/00
(52) U.S. Cl. ..................... 600/101; 348/82; 901/1; 901/47
(58) Field of Search .................. 600/101, 114, 600/160; 604/95.01; 901/1, 47; 348/82, 84, 85; 73/865.8

(56) References Cited

U.S. PATENT DOCUMENTS

| | | | |
|---|---|---|---|
| 4,852,391 A | | 8/1989 | Ruch et al. |
| 5,142,989 A | | 9/1992 | Suzumori et al. |
| 5,345,925 A | * | 9/1994 | Allred et al. ................ 600/114 |
| 5,493,988 A | | 2/1996 | Kollberg |
| 5,662,587 A | * | 9/1997 | Grundfest et al. .......... 600/114 |
| 6,071,234 A | | 6/2000 | Takada |
| 6,240,312 B1 | * | 5/2001 | Alfano et al. ................ 600/476 |
| 6,512,345 B2 | * | 1/2003 | Borenstein et al. ..... 318/568.12 |
| 6,648,814 B2 | | 11/2003 | Kim et al. |
| 2003/0017779 A1 | * | 1/2003 | Sakai .......................... 446/226 |
| 2003/0088152 A1 | | 5/2003 | Takada |
| 2003/0092353 A1 | * | 5/2003 | Liu ............................. 446/330 |
| 2003/0092964 A1 | | 5/2003 | Kim et al. |

* cited by examiner

Primary Examiner—John P. Leubecker
(74) Attorney, Agent, or Firm—Ostrolenk, Faber, Gerb & Soffen, LLP

(57) ABSTRACT

A micro robot that can move for itself is provided. The micro robot moves by moving a plurality of legs with a plurality of cams driven by a driving device, which comprises a micro robot body, a rotational shaft installed in the body and connected to driving device for generating rotational force, a plurality of cams positioned sequentially and connected to the rotational shaft having a certain phase difference centering around the rotational shaft, a plurality of legs installed in the body capable of moving by rotation of the cams, said legs being abutted to the respective cams at one end portion thereof and protruding outwardly from the body at the other end portion thereof, respectively and a locomotion device for moving the body.

22 Claims, 5 Drawing Sheets

MICRO ROBOT

FIELD OF THE INVENTION

The present invention relates to a micro robot and particularly, to a micro robot which can move for itself.

BACKGROUND OF THE INVENTION

A micro endoscope robot is a micro robot equipped with a camera for photographing internal organs, a micro twizer for biopsy of tissues, and a communication module for transmitting images of internal organ so that a doctor can examine the internal organs. If this kind of micro robot is developed, simple surgeries and medicine injections are possible as well as endoscopy of a stomach, small intestine or large intestines without giving much pain to a patient.

One of the existing endoscopes is called an inch-warm type micro robot. This micro robot moves by being supported on walls of a small intestine or large intestine with a damper which is inflated by air. This method has disadvantage that supporting force can not be provided enough in condition of an internal body which is slippery and easily transformed, or in case of raising supporting force, weak intestine walls can be damaged.

SUMMARY OF THE INVENTION

Therefore, an object of the present invention is to provide a micro robot which can crawl by itself to check inside of intestines, which is powered by positioning a plurality of cams which are positioned sequentially and connected to a rotational shaft having a certain phase difference centering around the rotational shaft and moving a plurality of legs installed by driving of the cams.

To achieve these and other advantages and in accordance with the purpose of the present invention, as embodied and broadly described herein, there is provided a micro robot comprising a micro robot body, a rotational shaft installed in the body and connected to driving means for generating rotational force, a plurality of cams positioned sequentially and connected to the rotational shaft having a certain phase difference centering around the rotational shaft, a plurality of legs installed in the body capable of moving by rotation of the cams, said legs being abutted to the respective cams at one end portion thereof and protruded outwardly from the body at the other end portion thereof, respectively and locomotion means for moving the body.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE PREFERRED EMBODIMENTS

Reference will now be made in detail to the preferred embodiments of the present invention, examples of which are Illustrated in the accompanying drawings.

Figure 1:
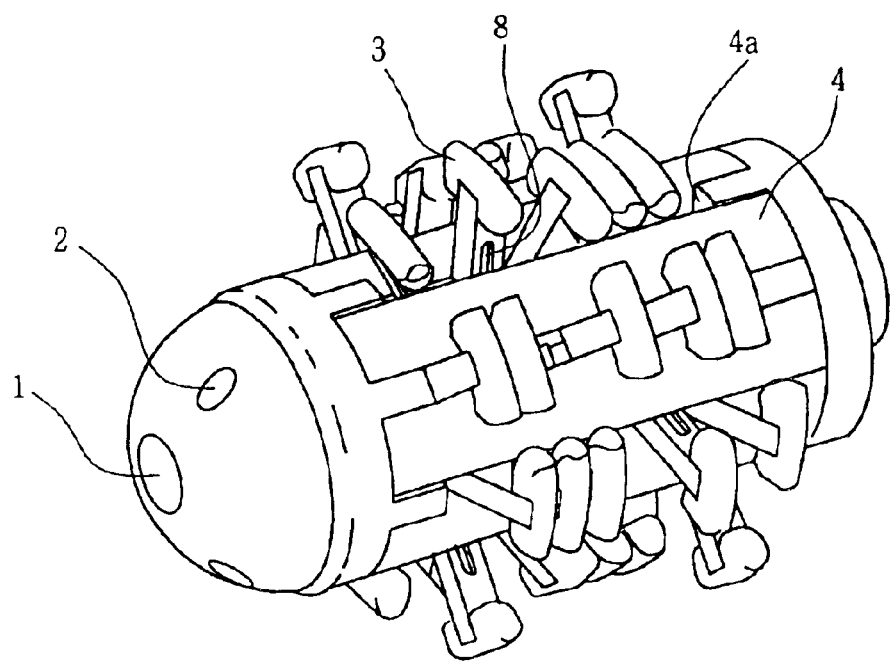
FIG. 1 is a perspective view showing an embodiment of a micro robot in accordance with the present invention.
Figure 2:
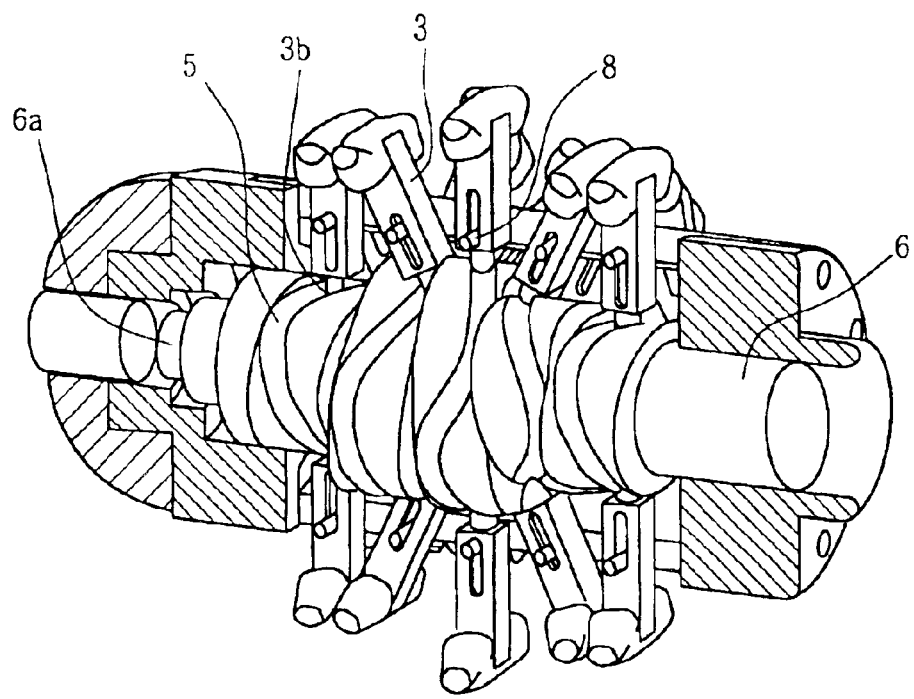
FIG. 2 illustrates an embodiment of a micro robot in accordance with the present invention.

FIG. 1 is a perspective view showing an embodiment of a micro robot and FIG. 2 illustrates an embodiment of a micro robot in accordance with the present invention.

As shown in FIGS. 1 and 2, a micro robot comprises a micro robot body 4 where a plurality of slots 4a are formed in a longitudinal direction of the body 4, a driving device 6 installed in the body 4, for generating rotational force. A rotational shaft 6a is installed in the body 4 and connected to the driving device 6. A plurality of cams 5 are positioned sequentially and connected to the rotational shaft 6a, the cams having a certain phase difference centering around the rotational shaft 6a in the body 4. A plurality of legs 3 penetrate the plurality of slots 4a and are installed on the body 4 by a leg installing unit so that the legs 3 are capable of moving, having inner ends 3b abutted to the respective cams 5. An elastic unit is installed in the respective legs 3 to generate restoring force. The micro robot also includes a locomotion device for moving the body 4.

As shown in FIG. 1 a camera 1, lighting source 2 etc. can be additionally mounted in the body 4.

Figure 3A:
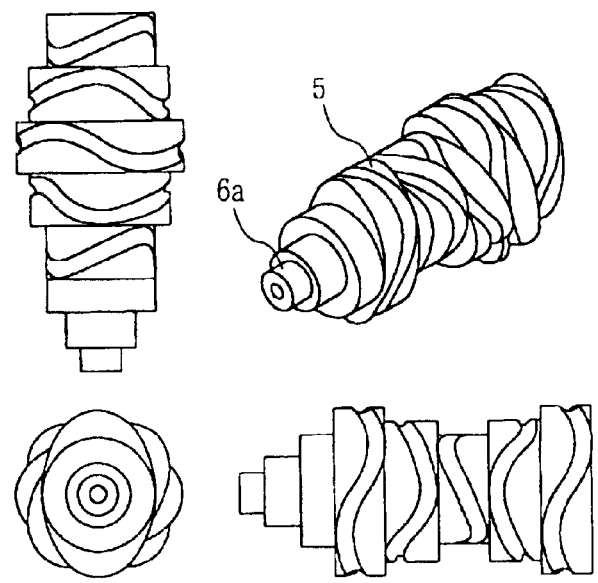
FIG. 3A is a perspective view showing a plurality of cams of the micro robot in an embodiment according to the present invention.
Figure 3B:
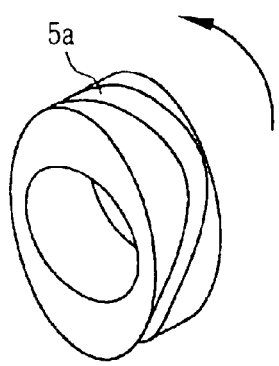
FIG. 3B is an enlarged perspective view showing the cams of the micro robot in an embodiment according to the present invention.
Figure 5:
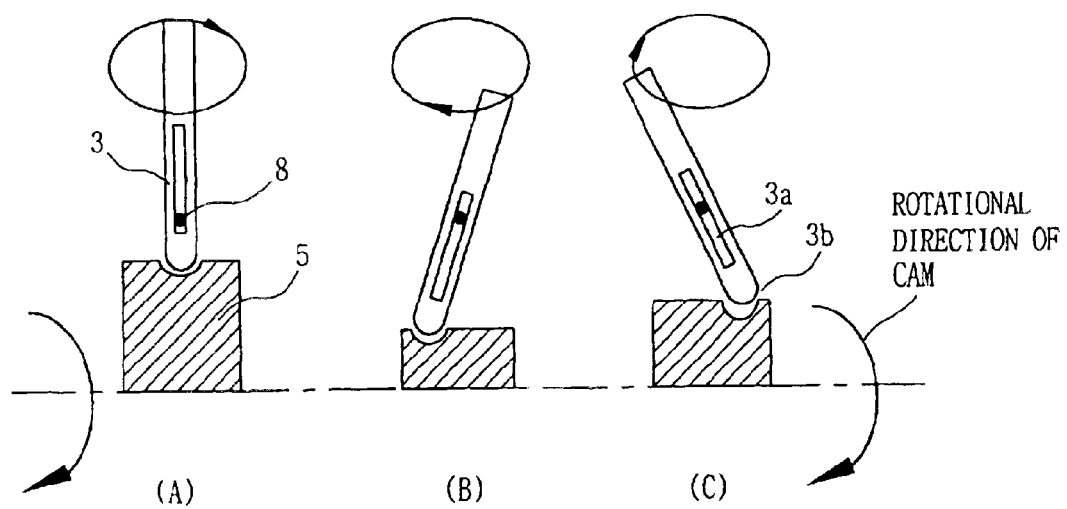
FIG. 5 illustrates an embodiment of movement of an end portion of the legs by compounding the cams and legs of the micro robot in accordance with the present invention.

As shown in FIGS. 3A and 3B and 5, the locomotion device has a certain angle with the rotational shaft 6a, an annular groove 5a is formed on a circumferential surface of the respective cams 5 and accordingly, the inner ends of the legs 3 are abutted to the groove 5a.

It is desirable that the groove 5a has a U-shape and the inner ends 3b of the legs 3 abutted to the groove 5a have a U-shape so that the inner ends 3b are fitted to the groove 5a The inner ends 3b of the legs 5 are not separated from the groove 5a, and are moved to contact the groove 5a.

Particularly, as shown in FIG. 3A, the plurality of cams 5 are sequentially combined to the rotational shaft 6a having a certain phase difference and the number of the cams 5 is formed as, for example, 5 steps, but the number can be either increased or decreased at need.

Also, as shown in FIG. 3A, the driving device 6 may be positioned inside the cams 5 thus to overcome the restriction of the space and reduce the length of the micro robot body 4.

Figure 4:
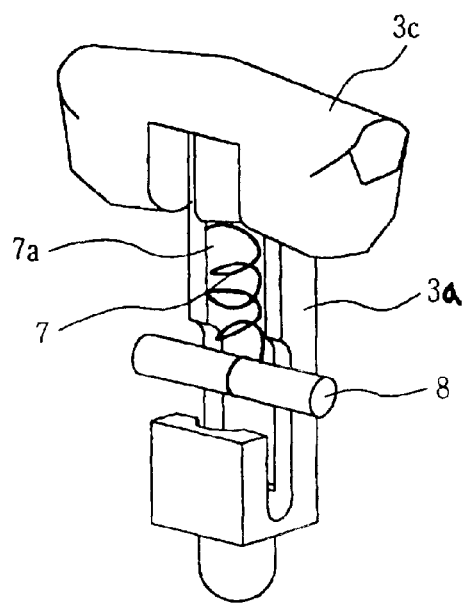
FIG. 4 is an enlarged perspective view of an embodiment of legs of the micro robot in accordance with the present invention.

As shown in FIG. 4, the elastic unit includes a cylindrical space 7a formed in a longitudinal direction of the legs 3, and a spring 7 inserted into the cylindrical space 7a in the legs 3. Both ends of the spring 7 are fixed by the outer end 3c of the legs 3 and a pin 8. By the elastic unit, the end 3b of the leg 3 abutted to the cam 5 and the cam 5 can be maintained in contact with the legs 3.

In case of the elastic unit, as shown in FIGS. 2 and 4, leg installing unit includes a slot 3a formed on a side surface of the leg 3 and the pin 8 penetrating the slot 3a and fixed to the body 4. By the pin 8, the outer end 3c of the leg 3 performs an elliptic movement when driving the cam 5.

Also, as shown in FIG. 4, the leg 3 has buffer members at each outer end 3b. It is desirable that each buffer member be made of silicon. The buffer member prevents the intestine from being damaged and adds driving force to the micro robot efficiently. It is desirable that the plurality of legs 3 be installed forming a certain angle radial-symmetrically around the rotational shaft 6a of the cam 5, for example several groups of legs 3 in row as shown in FIGS. 1 and 2.

As shown in FIG. 5, the elastic unit can be installed for binding the legs 3 abutted to the each cam 5 with an elastic body selectively. In this case, the elastic unit functions as a leg fixing unit to fix the legs 3 to the body 4 and accordingly, an additional leg installing unit is not required.

Operations of an embodiment of the micro robot in accordance with the present invention will be described as follows.

Firstly, rotation at force generated by the driving device 6 is transmitted to the plurality of cams 5 through the rotational shaft 6a and accordingly, the cams 5 start to rotate. The legs 3 abutted to the cams 5 perform a certain movement by rotation of the cams 5.

In case the elastic unit and fixing unit have the structure as shown in FIGS. 2 and 4, the outer ends 3c of the legs perform elliptic movements as shown in FIG. 5. The outer ends 3c of the legs are abutted to the intestine and move the micro robot by the elliptical movement.

By the way, the micro robot with the above structure has only a function of converting direction passively according to the environment. Efficient movement is difficult to be made at the portion of a curve forming an acute angle with only the passive direction conversion function. Therefore, active direction conversion is needed according to circumstances.

An exemplary embodiment of the present invention provides a micro robot which can convert direction actively, and another embodiment of the micro robot according to the present invention will be described in detail with reference to the accompanied drawings.

Figure 6:
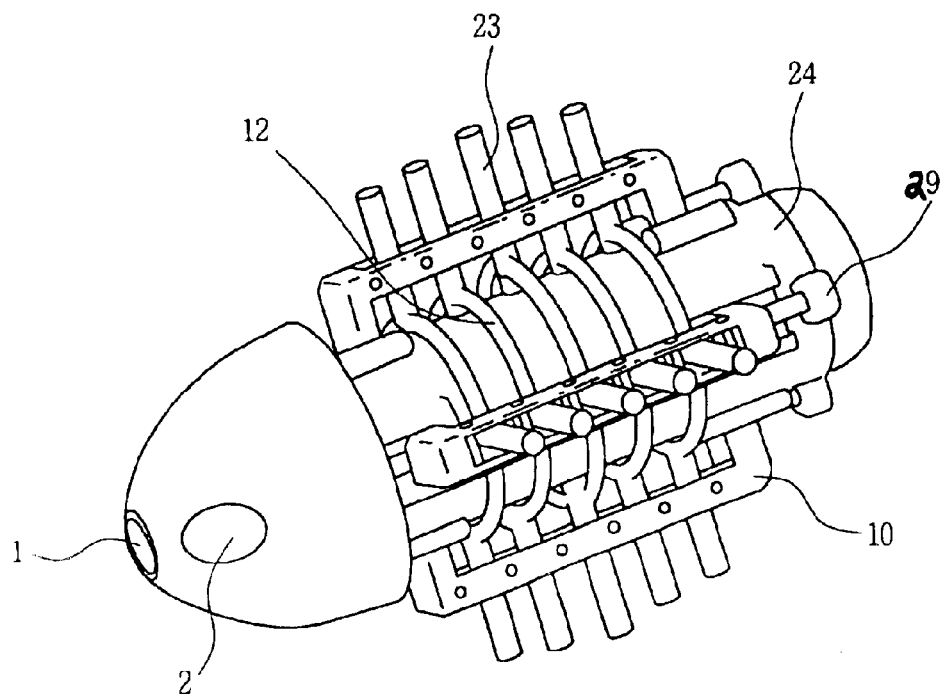
FIG. 6 is a perspective view showing another embodiment of the micro robot having a guide means in accordance with the present invention.
Figure 7:
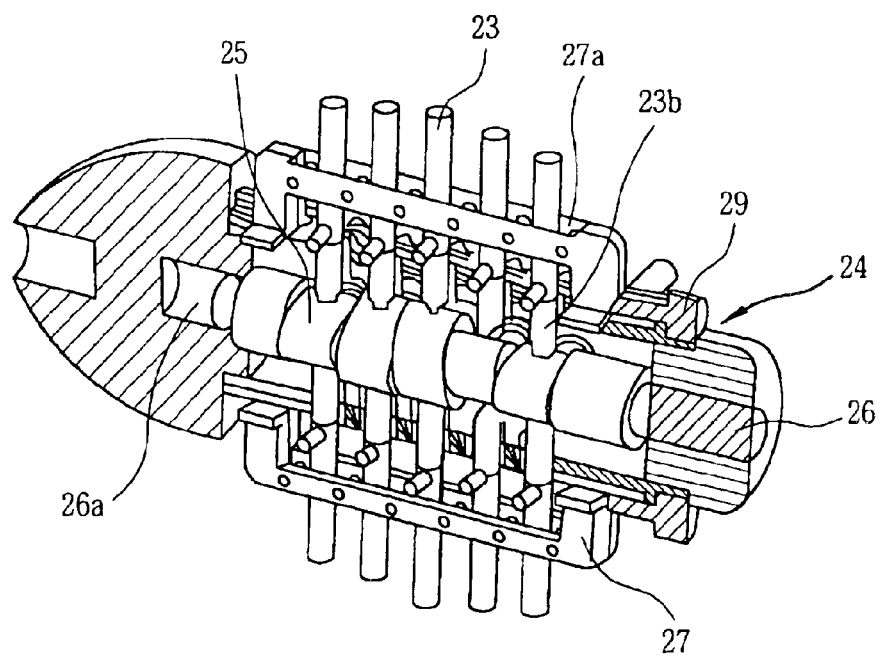
FIG. 7 illustrates another embodiment showing the inner portion of the micro robot having the guide means in accordance with the present invention.

FIG. 6 is a perspective view showing another embodiment of the micro robot having guide unit, and FIG. 7 illustrates another embodiment showing the inner portion of the micro robot having the guide unit in accordance with the present invention.

As shown in FIGS. 6 and 7, the micro robot comprises a micro robot body 24 where a plurality of slots (4a in FIG. 1) are formed in a longitudinal direction, a driving device 26 for generating rotational force in the body 24. A rotational shaft 26a is installed in the body 24 and connected to the driving device 26. A plurality of cams 25 are positioned sequentially and connected to the rotational shaft 26a having a certain phase difference centering around the rotational shaft 26a in the body 24. A plurality of legs 23 penetrate a plurality of slots 24a, respectively and installed on the body 24 so that the legs 23 are capable of moving, having an inner end 23b abutted to each cam 25. An elastic unit 12 is installed in the respective legs 23 to generate restoring force. The micro robot also includes a locomotion device for moving the body 24.

The locomotion device includes a plurality of lattices 27a, a guide unit having a guide 27 which performs linear movement in a longitudinal direction of the body 24 and a linear driving device 29 for driving the guide 27 and by penetrating the leg 23 in the respective lattices 27a thus to move the leg 23 according to the guidance of the guide unit.

As the linear driving device of the guide unit, a subminiature motor shape memory alloy (SMA) or a pneumatic cylinder can be used.

In case the locomotion device includes a guide unit, the legs 23 are installed abutted to the respective cams 25, with an elastic body, which is an elastic unit, at one end as shown in FIG. 7. In this case, a leg installing unit is not required to install the legs 23 to the body 24.

Also, the legs 23 are made of flexible silicon except for the end 23a abutted to the cams 25 thereby bending the legs 23 forwards or backwards by the guide 27 to prevent the intestine from being damaged.

As shown in FIG. 6, a camera, lighting source, etc. can be installed on the body 24.

It is desirable that the plurality of legs 23 be installed forming a certain angle radial-symmetrically around the rotational shaft 26a of the cams 25.

Particularly, as shown in FIG. 7, the plurality of the cams 25 are sequentially combined to the rotational shaft 26a having a certain phase difference and the number of the cams 25 is formed as 5 steps, but the number can be either increased or decreased at need.

Also, as shown in FIG. 7, the driving device 26 is positioned inside the cam 25 thus to overcome space restriction and reduce length.

The operation of the micro robot of another embodiment of the present invention will be described as follows.

Figure 8:
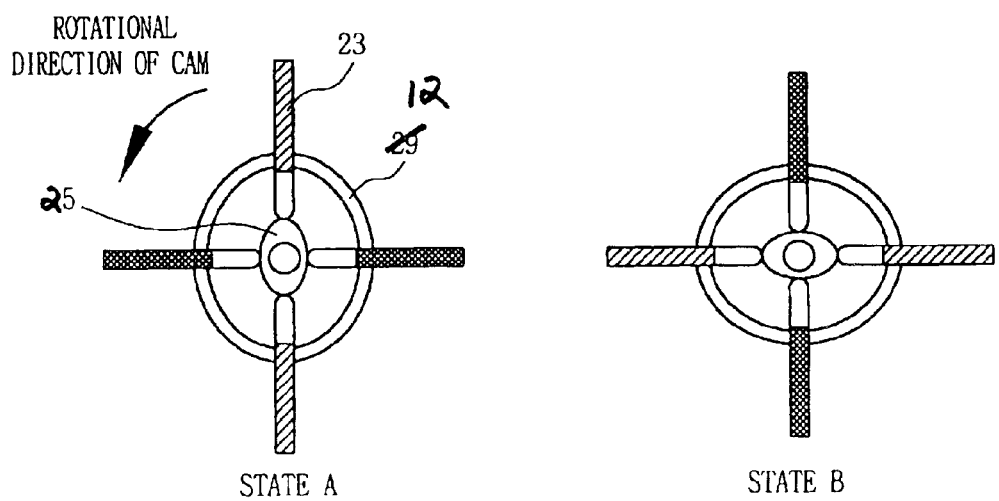
FIG. 8 illustrates another embodiment of movement of legs bound by a U-shape elastic means having the guide means in accordance with the present invention.

Firstly, rotational force generated by driving of the driving device 26 is transmitted to the plurality of cams 25 connected to the rotational shaft 26a through the rotational shaft 26a and accordingly, the cams 25 start to rotate. As shown in FIG. 8, the legs 23 abutted to the cams 25 perform a certain movement by the rotation of the cams 25.

The legs 23 made of flexible silicon are bent by the guide 27 forwards or backwards. Namely, the flexible legs 23 perform only linear movement by rotation of the cams 25 and the direction of forward or backward is determined by the guide 27.

In FIG. 8, the operations of the cams 25 and the flexible legs 23 are illustrated, and reference numerals A and B illustrate the position of the legs having the cam phase difference of 90°.

At state A, a pair of legs 23 which stand horizontally are positioned farthest from the rotational shaft 26a of the cams 25 and a pair of legs 23 which lie vertically are positioned closest from the rotational shaft 26a. The difference of the position forms straight displacement.

At state B, namely, if the cams 25 rotate 90°, the distance between the horizontal pair of legs 23 and the cams 25 of the vertical pair of legs 23 is opposite to the distance at state A.

At this time, the legs 23 positioned in a long distance are restored by the elastic body 12 which binds the legs 23 in a round form. Namely, the elastic body 12 which is attached to the legs 23 which are far from the center of the cam 25 pulls the legs 23. Therefore, the legs 23 can perform reciprocating movement without installing an apparatus such as a spring in a small space.

Figure 9:
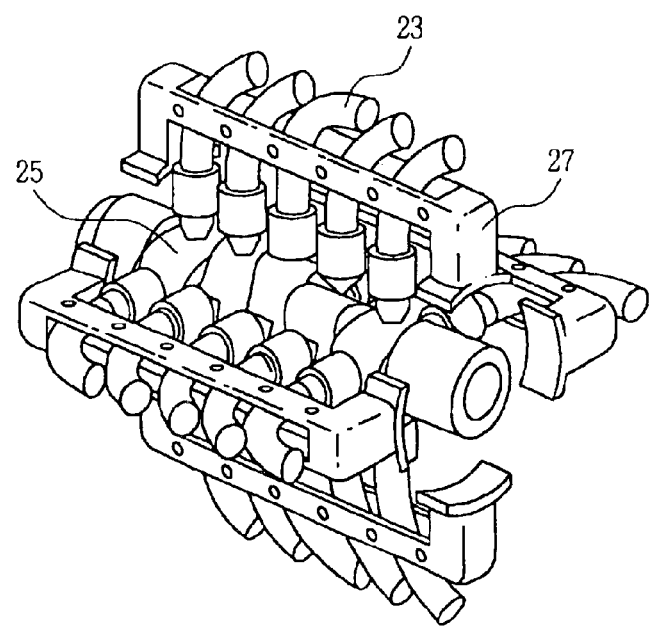
FIG. 9 is a perspective view showing another embodiment of folded flexible legs of the micro robot having the guide means by the guide in accordance with the present invention.

As shown in FIG. 9, by the operation of the guide 27, the direction to which the flexible legs 23 are bent is determined. The guide 27 can be controlled independently by the linear driving device 26, and the direction can be converted in the necessary direction as well as forward or backward along with the four combinations.

For the composition of the micro robot of the second embodiment, the elastic unit may be formed with a cylindrical space in the direction of the length of the legs and in the elastic unit, and the spring can be positioned selectively as shown in FIG. 4. The spring is fixed by the outer end of the body of the legs and the pin. By the elastic unit, the ends of the legs which are abutted to the cam and are maintained in contact with the cam. In this case, the leg installing unit forms a through hole in the form of a rectangle on the side surface of the legs and the pin which protrudes the through hole can be fixed on the body.

In the above case, as shown in FIG. 4, the leg has an end portion of a buffer member at the outer end. It is desirable that the buffer member is made of silicon. The buffer member can prevent damage to the intestine and can add driving force to the micro robot.

Figure 3C:
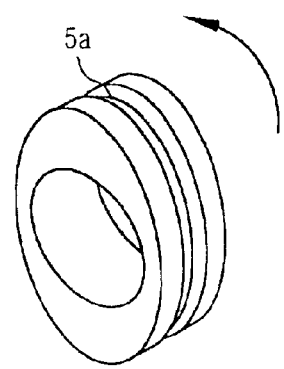
FIG. 3C is an enlarged perspective view showing another example of the cams of the micro robot in an embodiment according to the present invention.

Also, for the composition of the micro robot of the second embodiment, as shown in FIGS. 3A, 3B and 5, the locomotion device has a certain angle with respect to the rotational shaft of the cam selectively, an annular groove is formed on the circumferential surface of the cam and accordingly, the inner end of the leg can be abutted to the groove. In this case, the round groove can be vertical to the rotational shaft, as shown in FIG. 3C. It is desirable that the groove becomes U-shape and the inner end of the leg abutted to the groove is also a U-shape. The inner end of the leg is not separated from the groove and follows the groove by the movement device.

The present invention is described on the basis of desirable embodiments but there can be more micro robots which do not stray from the gist of the present invention.

As described above, in accordance with the present invention, the micro robot moves for itself by moving the plurality of legs by the plurality of cams driven by the driving device and accordingly, it can move the plurality of legs in a small space such as the large intestine using only a driving apparatus in the internal body.

Also, in accordance with the present invention, the micro robot shows proper mobility in a hard pipe as well as in the circumstance which is slippery and easily transformed such as the internal portion of the intestines.

Therefore, the micro robot can be used for endoscopy or surgery for examining or diagnosing the large intestine and small intestine using a more simple and efficient structure. The manufacturing is easy and the cost can be reduced. The general size is miniaturized and pain of patients can be also eased.

Also, the present invention can provide a new method for a moving apparatus which can move in a pipe, as well as for a moving apparatus for an endoscope.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A micro robot, comprising:
   a micro robot body;
   a rotational shaft installed in the body and connected to driving means for generating rotational force;
   a plurality of cams positioned sequentially and connected to the rotational shaft having a certain phase difference centering around the rotational shaft;
   a plurality of legs installed in the body capable of moving by rotation of the cams, said legs being abutted to the respective cams at one end portion thereof and protruded outwardly from the body at the other end portion thereof, respectively; and
   locomotion means for moving the body.

2. The micro robot of claim 1, wherein the locomotion means includes an annular groove formed on a circumferential surface of the respective cams having a certain angle with the rotational shaft, and abutted to one end portion of each one of the legs.

3. The micro robot of claim 1, wherein the locomotion means includes guide means having a guide which a plurality of lattices are formed in and performs linear movement in a longitudinal direction of the body, and linear driving means for driving the guide, and each one of the legs penetrates the corresponding lattice for moving the legs according to guidance of the guide means.

4. The micro robot of claim 3, wherein the linear driving means for driving the guide is an electric motor.

5. The micro robot of claim 3, wherein the linear driving means for driving the guide is shape memory alloy.

6. The micro robot of claim 3, wherein the linear driving means for driving the guide is a pneumatic cylinder.

7. The micro robot of claim 3, wherein the locomotion means includes an annular groove formed on a circumferential surface having a certain angle with the rotational shaft, and abutted to one end portion of each one of the legs.

8. The micro robot of claim 7, wherein the annular groove is vertical to the rotational shaft.

9. The micro robot of claim 7, wherein the groove has U-shape and the one end portion of the leg abutted to the groove has U-shape for being fitted to the groove.

10. The micro robot of claim 1, wherein a cylindrical space is formed within each one of the legs in a longitudinal direction of the leg and a spring is inserted in the cylindrical space.

11. The micro robot of claim 10, wherein a slot is formed in each one of the legs and a pin fixed to the body penetrates the slot.

12. The micro robot of claim 11, wherein both ends of the spring are respectively fixed to the other end portion of the respective leg and the pin.

13. The micro robot of claim 11, wherein the other end portion of the leg has a buffer member.

14. The micro robot of claim 13, wherein the buffer member is made of silicon.

15. The micro robot of claim 1, wherein the legs abutted to the respective cams are bound with a circular elastic body.

16. The micro robot of claim 15, wherein the legs are flexible.

17. The micro robot of claim 16, wherein the legs are made of silicon.

18. The micro robot of claim 1, wherein a pair of legs are positioned in the respective cams.

19. The micro robot of claim 1, wherein the plurality of legs positioned in the respective cams in a uniform angular interval and radial-symmetrically around the rotational shaft.

20. The micro robot of claim 1, wherein the driving means is positioned inside the cam.

21. The micro robot of claim 1, wherein a plurality of slots are formed and the legs penetrates the respective slots.

22. The micro robot of claim 1, wherein a camera device and a lighting source are installed within the body.

* * * * *